(12) United States Patent
Bando et al.

(10) Patent No.: US 9,303,251 B2
(45) Date of Patent: Apr. 5, 2016

(54) RECOMBINANT BACULOVIRUS AND USE THEREOF

(71) Applicant: SYSMEX CORPORATION, Kobe-shi, Hyogo (JP)

(72) Inventors: Takahiko Bando, Sanda (JP); Mutsumi Sugai, Fujimino (JP)

(73) Assignee: SYSMEX CORPORATION, Kobe-shi (JP)

( * ) Notice: Subject to any disclaimer, the term of this patent is extended or adjusted under 35 U.S.C. 154(b) by 134 days.

(21) Appl. No.: 14/227,747

(22) Filed: Mar. 27, 2014

(65) Prior Publication Data

US 2014/0295496 A1 Oct. 2, 2014

(30) Foreign Application Priority Data

Mar. 29, 2013 (JP) ................. 2013-072021

(51) Int. Cl.

| | | |
|---|---|---|
| C12N 15/09 | (2006.01) | |
| C12N 15/866 | (2006.01) | |
| C12N 9/74 | (2006.01) | |
| C07K 14/745 | (2006.01) | |
| C12P 21/02 | (2006.01) | |
| C12N 9/02 | (2006.01) | |
| C12N 9/88 | (2006.01) | |
| C12N 15/86 | (2006.01) | |
| C12N 9/64 | (2006.01) | |

(52) U.S. Cl.
CPC ............ *C12N 9/6429* (2013.01); *C07K 14/745* (2013.01); *C12N 9/0036* (2013.01); *C12N 9/644* (2013.01); *C12N 9/6432* (2013.01); *C12N 9/6437* (2013.01); *C12N 9/6464* (2013.01); *C12N 9/88* (2013.01); *C12N 15/86* (2013.01); *C12P 21/02* (2013.01); *C12Y 106/05002* (2013.01); *C12Y 401/0109* (2013.01); *A01K 2207/05* (2013.01); *A01K 2227/706* (2013.01); *A01K 2267/01* (2013.01); *C12N 2710/14143* (2013.01); *Y02P 20/52* (2015.11)

(58) Field of Classification Search
None
See application file for complete search history.

(56) References Cited

U.S. PATENT DOCUMENTS

| | | |
|---|---|---|
| 2005/0164367 A1 | 7/2005 | Fenge et al. |
| 2009/0100533 A1 | 4/2009 | Steenstrup |

OTHER PUBLICATIONS

Jian-Ke Tie et al., "Functional study of the vitamin K cycle in mammalian cells," Blood, 2011, pp. 2967-2974, vol. 117, No. 10.
Susumu Maeda, "Gene Transfer Vectors of a Baculovirus, Bombyx Mori Nuclear Polyhedrosis Virus, and Their Use for Expression of Foreign Genes in Insect Cells," Invertebrate Cell System Applications, 1989, pp. 167-181, vol. 1.

*Primary Examiner* — Marsha Tsay
(74) *Attorney, Agent, or Firm* — Sughrue Mion, PLLC

(57) ABSTRACT

The present invention provides a recombinant baculovirus. The baculovirus has a genome into which a gene encoding γ-glutamyl carboxylase (GGCX) and a gene encoding DT-diaphorase (NQO1) are incorporated.
The present invention further provides a method for producing a recombinant vitamin K-dependent protein by using the recombinant baculovirus.

17 Claims, 4 Drawing Sheets

WB: ANTI PTH Ab

IP: ANTI GLA DOMAIN Ab
WB: ANTI PTH Ab

WB: ANTI hFX Ab

IP: ANTI GLA DOMAIN Ab
WB: ANTI hFX Ab

SEQUENCE LISTING

<160> NUMBER OF SEQ ID NOS: 15

<210> SEQ ID NO 1
<211> LENGTH: 758
<212> TYPE: PRT
<213> ORGANISM: Homo sapiens

<400> SEQUENCE: 1

Met Ala Val Ser Ala Gly Ser Ala Arg Thr Ser Pro Ser Ser Asp Lys
1               5                   10                  15

Val Gln Lys Asp Lys Ala Glu Leu Ile Ser Gly Pro Arg Gln Asp Ser
            20                  25                  30

```
Arg Ile Gly Lys Leu Leu Gly Phe Glu Trp Thr Asp Leu Ser Ser Trp
            35                  40                  45

Arg Arg Leu Val Thr Leu Leu Asn Arg Pro Thr Asp Pro Ala Ser Leu
 50                  55                  60

Ala Val Phe Arg Phe Leu Phe Gly Phe Leu Met Val Leu Asp Ile Pro
 65                  70                  75                  80

Gln Glu Arg Gly Leu Ser Ser Leu Asp Arg Lys Tyr Leu Asp Gly Leu
                    85                  90                  95

Asp Val Cys Arg Phe Pro Leu Leu Asp Ala Leu Arg Pro Leu Pro Leu
                100                 105                 110

Asp Trp Met Tyr Leu Val Tyr Thr Ile Met Phe Leu Gly Ala Leu Gly
            115                 120                 125

Met Met Leu Gly Leu Cys Tyr Arg Ile Ser Cys Val Leu Phe Leu Leu
            130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175

Asn His Tyr Trp Ser Val Asp Gly Leu Leu Asn Ala His Arg Arg Asn
            180                 185                 190

Ala His Val Pro Leu Trp Asn Tyr Ala Val Leu Arg Gly Gln Ile Phe
            195                 200                 205

Ile Val Tyr Phe Ile Ala Gly Val Lys Lys Leu Asp Ala Asp Trp Val
            210                 215                 220

Glu Gly Tyr Ser Met Glu Tyr Leu Ser Arg His Trp Leu Phe Ser Pro
225                 230                 235                 240

Phe Lys Leu Leu Leu Ser Glu Glu Leu Thr Ser Leu Leu Val Val His
                245                 250                 255

Trp Gly Gly Leu Leu Leu Asp Leu Ser Ala Gly Phe Leu Leu Phe Phe
                260                 265                 270

Asp Val Ser Arg Ser Ile Gly Leu Phe Phe Val Ser Tyr Phe His Cys
            275                 280                 285

Met Asn Ser Gln Leu Phe Ser Ile Gly Met Phe Ser Tyr Val Met Leu
            290                 295                 300

Ala Ser Ser Pro Leu Phe Cys Ser Pro Glu Trp Pro Arg Lys Leu Val
305                 310                 315                 320

Ser Tyr Cys Pro Gln Arg Leu Gln Gln Leu Leu Pro Leu Lys Ala Ala
                325                 330                 335

Pro Gln Pro Ser Val Ser Cys Val Tyr Lys Arg Ser Arg Gly Lys Ser
                340                 345                 350

Gly Gln Lys Pro Gly Leu Arg His Gln Leu Gly Ala Ala Phe Thr Leu
            355                 360                 365

Leu Tyr Leu Leu Glu Gln Leu Phe Leu Pro Tyr Ser His Phe Leu Thr
            370                 375                 380

Gln Gly Tyr Asn Asn Trp Thr Asn Gly Leu Tyr Gly Tyr Ser Trp Asp
385                 390                 395                 400

Met Met Val His Ser Arg Ser His Val Lys Ile Thr Tyr Arg
                405                 410                 415

Asp Gly Arg Thr Gly Glu Leu Gly Tyr Leu Asn Pro Gly Val Phe Thr
            420                 425                 430

Gln Ser Arg Arg Trp Lys Asp His Ala Asp Met Leu Lys Gln Tyr Ala
            435                 440                 445
```

```
Thr Cys Leu Ser Arg Leu Leu Pro Lys Tyr Asn Val Thr Glu Pro Gln
    450                 455                 460

Ile Tyr Phe Asp Ile Trp Val Ser Ile Asn Asp Arg Phe Gln Gln Arg
465                 470                 475                 480

Ile Phe Asp Pro Arg Val Asp Ile Val Gln Ala Ala Trp Ser Pro Phe
                485                 490                 495

Gln Arg Thr Ser Trp Val Gln Pro Leu Leu Met Asp Leu Ser Pro Trp
            500                 505                 510

Arg Ala Lys Leu Gln Glu Ile Lys Ser Ser Leu Asp Asn His Thr Glu
        515                 520                 525

Val Val Phe Ile Ala Asp Phe Pro Gly Leu His Leu Glu Asn Phe Val
    530                 535                 540

Ser Glu Asp Leu Gly Asn Thr Ser Ile Gln Leu Leu Gln Gly Glu Val
545                 550                 555                 560

Thr Val Glu Leu Val Ala Glu Gln Lys Asn Gln Thr Leu Arg Glu Gly
                565                 570                 575

Glu Lys Met Gln Leu Pro Ala Gly Glu Tyr His Lys Val Tyr Thr Thr
            580                 585                 590

Ser Pro Ser Pro Ser Cys Tyr Met Tyr Val Tyr Val Asn Thr Thr Glu
        595                 600                 605

Leu Ala Leu Glu Gln Asp Leu Ala Tyr Leu Gln Glu Leu Lys Glu Lys
    610                 615                 620

Val Glu Asn Gly Ser Glu Thr Gly Pro Leu Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Gln Arg Leu Gln Glu Ile Glu Arg Arg
            660                 665                 670

Arg Asn Thr Pro Phe His Glu Arg Phe Phe Arg Phe Leu Leu Arg Lys
        675                 680                 685

Leu Tyr Val Phe Arg Arg Ser Phe Leu Met Thr Cys Ile Ser Leu Arg
    690                 695                 700

Asn Leu Ile Leu Gly Arg Pro Ser Leu Glu Gln Leu Ala Gln Glu Val
705                 710                 715                 720

Thr Tyr Ala Asn Leu Arg Pro Phe Glu Ala Val Gly Glu Leu Asn Pro
                725                 730                 735

Ser Asn Thr Asp Ser Ser His Ser Asn Pro Pro Glu Ser Asn Pro Asp
            740                 745                 750

Pro Val His Ser Glu Phe
        755

<210> SEQ ID NO 2
<211> LENGTH: 274
<212> TYPE: PRT
<213> ORGANISM: Homo sapiens

<400> SEQUENCE: 2

Met Val Gly Arg Arg Ala Leu Ile Val Leu Ala His Ser Glu Arg Thr
1               5                   10                  15

Ser Phe Asn Tyr Ala Met Lys Glu Ala Ala Ala Ala Leu Lys Lys
            20                  25                  30

Lys Gly Trp Glu Val Val Glu Ser Asp Leu Tyr Ala Met Asn Phe Asn
        35                  40                  45

Pro Ile Ile Ser Arg Lys Asp Ile Thr Gly Lys Leu Lys Asp Pro Ala
    50                  55                  60
```

```
Asn Phe Gln Tyr Pro Ala Glu Ser Val Leu Ala Tyr Lys Glu Gly His
 65                  70                  75                  80

Leu Ser Pro Asp Ile Val Ala Glu Gln Lys Lys Leu Glu Ala Ala Asp
                 85                  90                  95

Leu Val Ile Phe Gln Phe Pro Leu Gln Trp Phe Gly Val Pro Ala Ile
            100                 105                 110

Leu Lys Gly Trp Phe Glu Arg Val Phe Ile Gly Glu Phe Ala Tyr Thr
        115                 120                 125

Tyr Ala Ala Met Tyr Asp Lys Gly Pro Phe Arg Ser Lys Lys Ala Val
    130                 135                 140

Leu Ser Ile Thr Thr Gly Gly Ser Gly Ser Met Tyr Ser Leu Gln Gly
145                 150                 155                 160

Ile His Gly Asp Met Asn Val Ile Leu Trp Pro Ile Gln Ser Gly Ile
                165                 170                 175

Leu His Phe Cys Gly Phe Gln Val Leu Glu Pro Gln Leu Thr Tyr Ser
            180                 185                 190

Ile Gly His Thr Pro Ala Asp Ala Arg Ile Gln Ile Leu Glu Gly Trp
        195                 200                 205

Lys Lys Arg Leu Glu Asn Ile Trp Asp Glu Thr Pro Leu Tyr Phe Ala
210                 215                 220

Pro Ser Ser Leu Phe Asp Leu Asn Phe Gln Ala Gly Phe Leu Met Lys
225                 230                 235                 240

Lys Glu Val Gln Asp Glu Lys Asn Lys Phe Gly Leu Ser Val
                245                 250                 255

Gly His His Leu Gly Lys Ser Ile Pro Thr Asp Asn Gln Ile Lys Ala
                260                 265                 270

Arg Lys

<210> SEQ ID NO 3
<211> LENGTH: 24
<212> TYPE: PRT
<213> ORGANISM: Artificial Sequence
<220> FEATURE:
<223> OTHER INFORMATION: Synthetic signal peptide

<400> SEQUENCE: 3

Met Ala His Tyr Arg Gly Leu Gln Leu Pro Gly Cys Leu Ala Leu Ala
1               5                   10                  15

Ala Leu Cys Ser Leu Tyr His Ser
            20

<210> SEQ ID NO 4
<211> LENGTH: 19
<212> TYPE: PRT
<213> ORGANISM: Artificial Sequence
<220> FEATURE:
<223> OTHER INFORMATION: Synthetic signal peptide

<400> SEQUENCE: 4

Met Arg Leu Thr Leu Phe Ala Phe Val Leu Ala Val Cys Ala Leu Ala
1               5                   10                  15

Ser Asn Ala

<210> SEQ ID NO 5
<211> LENGTH: 16
<212> TYPE: PRT
<213> ORGANISM: Artificial Sequence
<220> FEATURE:
<223> OTHER INFORMATION: Synthetic signal peptide
```

<400> SEQUENCE: 5

Met Arg Val Leu Val Leu Leu Ala Cys Leu Ala Ala Ala Ser Asn Ala
1               5                   10                  15

<210> SEQ ID NO 6
<211> LENGTH: 31
<212> TYPE: DNA
<213> ORGANISM: Artificial Sequence
<220> FEATURE:
<223> OTHER INFORMATION: Synthetic oligonucleotide primer

<400> SEQUENCE: 6
ggggtaccat ggcggtgtct gccgggtccg c                           31

<210> SEQ ID NO 7
<211> LENGTH: 30
<212> TYPE: DNA
<213> ORGANISM: Artificial Sequence
<220> FEATURE:
<223> OTHER INFORMATION: Synthetic oligonucleotide primer

<400> SEQUENCE: 7
gctctagaga actctgagtg gacaggatca                             30

<210> SEQ ID NO 8
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 8
gaagatctat ggtcggcaga agagcactga tcgta                       35

<210> SEQ ID NO 9
<211> LENGTH: 36
<212> TYPE: DNA
<213> ORGANISM: Artificial Sequence
<220> FEATURE:
<223> OTHER INFORMATION: Synthetic oligonucleotide primer

<400> SEQUENCE: 9
gctctagatt ttctagcttt gatctggttg tcagtt                      36

<210> SEQ ID NO 10
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 10
ggggtaccat gggcagcacc tgggggagcc ct                          32

<210> SEQ ID NO 11
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 11
gctctagatc agtgcctctt agccttgccc tg                          32

-continued

```
<210> SEQ ID NO 12
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 12
aaggtacccg gggatccatg gggcgcccac tg                                32

<210> SEQ ID NO 13
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 13
aatctagatc actttaatgg agaggacgtt at                                32

<210> SEQ ID NO 14
<211> LENGTH: 32
<212> TYPE: DNA
<213> ORGANISM: Artificial Sequence
<220> FEATURE:
<223> OTHER INFORMATION: Synthetic oligonucleotide primer

<400> SEQUENCE: 14
aagaattcat ggccaacacc ttcttggagg ag                                32

<210> SEQ ID NO 15
<211> LENGTH: 35
<212> TYPE: DNA
<213> ORGANISM: Artificial Sequence
<220> FEATURE:
<223> OTHER INFORMATION: Synthetic oligonucleotide primer

<400> SEQUENCE: 15
aatctagact actctccaaa ctgatcaatg acctt                             35
```

US 9,303,251 B2

RECOMBINANT BACULOVIRUS AND USE THEREOF

FIELD OF THE INVENTION

The present invention relates to a recombinant baculovirus and a kit for producing a recombinant vitamin K-dependent protein that contains the recombinant baculovirus. The present invention also relates to a host cell infected with the recombinant baculovirus. Further, the present invention relates to a method for producing a recombinant vitamin K-dependent protein.

BACKGROUND

Vitamin K is a cofactor of γ-glutamyl carboxylase (GGCX) which has a role in post-translational modification of various types of vitamin K-dependent proteins. Predetermined glutamic residues in various vitamin K-dependent proteins are carboxylated by GGCX in the presence of vitamin K, resulting in conversion into γ-carboxyglutamic acid (Gla). The γ-glutamyl carboxylation is known to be very important for biological functions of the vitamin K-dependent proteins (for example, blood coagulation, bone metabolism, and signal transduction). For example, the blood coagulation factor II (prothrombin) which is a kind of the vitamin K-dependent proteins or the factor X can be bound to phospholipids of the cell membrane (the site for the coagulation reaction) by γ-glutamyl carboxylation. As a result, the activation responses from other factors are received.

Vitamin K-dependent blood coagulation factor such as the factor II or factor X is mainly prepared by using the plasma from human or bovine as a raw material. However, the incorporation of infectious materials into the raw material or a difference between the production lots causes a problem. Therefore, methods for producing a vitamin K-dependent blood coagulation factor by the recombinant DNA technique using a mammalian cell have been recently studied and developed.

However, it is known that the vitamin K-dependent blood coagulation factor obtained by the expression system using a mammalian cell is not completely in the γ-glutamyl carboxylated form. It is generally difficult to activate the coagulation factor which is not in the γ-glutamyl carboxylated form. Accordingly, it is desirable that the recombinant vitamin K-dependent blood coagulation factor is sufficiently in the γ-glutamyl carboxylated form when obtained in the protein expression system, from the viewpoint of industrial application. Therefore, a method for producing a γ-glutamyl carboxylated protein, comprising co-expressing a vitamin K-dependent protein and GGCX in the expression system using a mammalian cell has been developed (refer to US Pub 2005/164367).

On the other hand, in addition to GGCX, vitamin K epoxide reductase (VKOR) and DT-diaphorase (also referred to as "NAD(P)H-dependent quinone oxidoreductase 1"; NOQ1) are known to be involved in the γ-glutamyl carboxylation of the vitamin K-dependent protein (refer to Tie J-K. et al., Blood. vol. 117, and p. 2967-2974 (2011)). Here, the enzyme which is directly involved in the γ-glutamyl carboxylation is GGCX, while VKOR and NQO1 are enzymes which are involved in the recycling of vitamin K. In recent years, a method for producing a γ-glutamyl carboxylated protein, comprising co-expressing a vitamin K-dependent protein, GGCX, and VKOR in the expression system using a mammalian cell has been developed (refer to US Pub 2009/100533).

SUMMARY OF THE INVENTION

Since the expression system using a mammalian cell is used in both of the methods, the yield of the γ-glutamyl carboxylated protein is very low and the production cost is also high from the viewpoint of industrial-scale production.

On the other hand, the abundant expression of a desired protein in the expression system using *Escherichia coli* is expected. However, it is known that the expressed proteins are not post-translationally modified. Further, it is also known that when proteins having a complicated structure are expressed, almost all of the proteins become insoluble aggregates. Furthermore, it is expected to express the protein which is post-translationally modified similarly to the native form protein in the conventional expression system using a lepidopteran insect. However, preliminary experiments by the present inventors have shown that almost all of the vitamin K-dependent proteins expressed in *Bombyx mori* are not in the γ-glutamyl carboxylated form.

In view of the above circumstances, the present inventors have aimed at providing a method for producing a recombinant vitamin K-dependent protein which satisfies both the condition where a vitamin K-dependent protein can be produced simply and in a large amount and the condition where the resulting vitamin K-dependent protein is sufficiently in the γ-glutamyl carboxylated form.

The present inventors have found that the vitamin K-dependent protein can be obtained simply and in a large amount by a lepidopteran expression system using a recombinant baculovirus into which a gene encoding GGCX and a gene encoding NQO1 are incorporated and a recombinant baculovirus into which a gene encoding a vitamin K-dependent protein is incorporated, and the resulting vitamin K-dependent protein is sufficiently in the γ-glutamyl carboxylated form. Thus, they have completed the present invention.

The present invention provides a recombinant baculovirus. Into a genome of the baculovirus, a gene encoding γ-glutamyl carboxylase (GGCX) and a gene encoding DT-diaphorase (NQO1) are incorporated.

The present invention provides a method for producing a recombinant vitamin K-dependent protein. The method comprises expressing a γ-glutamyl carboxylated vitamin K-dependent protein in a lepidopteran insect or cultured cell of the lepidopteran insect using a recombinant baculovirus. A gene encoding GGCX and a gene encoding NQO1 are incorporated into a genome of the baculovirus used in this method.

DETAILED DESCRIPTION OF PREFERRED EMBODIMENTS

Figure 1:
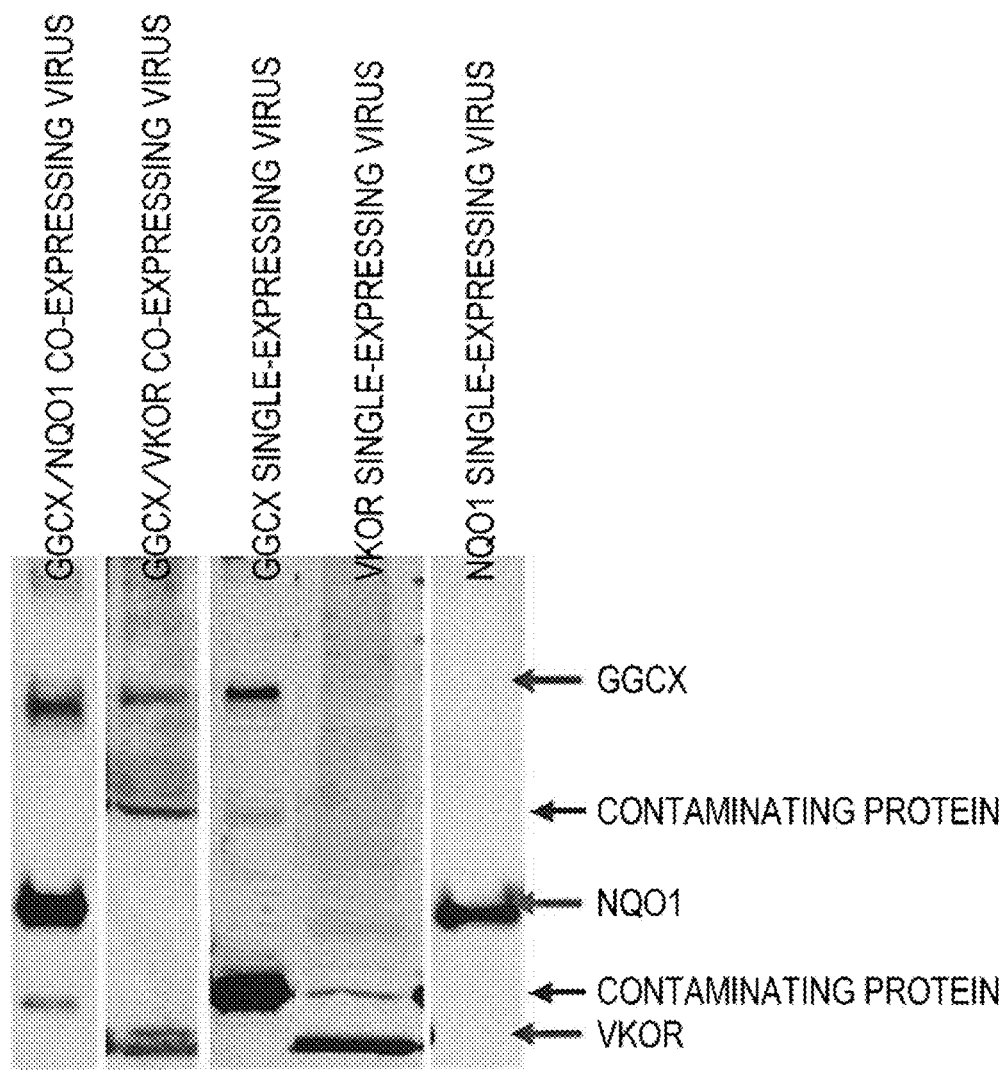
FIG. 1 shows photographs illustrating the expression levels of each of proteins in *Bombyx mori*-derived cultured cells infected with recombinant baculoviruses for singly expressing GGCX, NQO1, and VKOR or co-expressing two of them.

The preferred embodiments of the present invention will be described hereinafter with reference to the drawings.

A gene encoding GGCX and a gene encoding NQO1 are incorporated into the recombinant baculovirus of the present invention, and it is possible to co-express GGCX and NQO1 in a lepidopteran insect or cultured cell of the insect. The recombinant baculovirus of the present invention is appropriately used in the case of expressing a γ-glutamyl carboxylated vitamin K-dependent protein in a lepidopteran insect or cultured cells of the insect. That is, a lepidopteran insect or cultured cell of the insect is infected with the recombinant baculovirus of the present invention and a recombinant baculovirus into which a desired gene encoding a vitamin K-dependent protein is incorporated so that the γ-glutamyl carboxylated vitamin K-dependent protein can be expressed in the lepidopteran insect or cultured cell thereof in a large amount.

The term "vitamin K-dependent protein" used herein means a protein in which predetermined glutamic residues are carboxylated by GGCX in the presence of vitamin K, resulting in conversion into Gla. Examples of the protein include vitamin K-dependent blood coagulation factor, bone Gla protein, matrix Gla protein, growth arrest-specific protein 6, and Acanthophiinae FXa-like protein. Further, the vitamin K-dependent blood coagulation factor is not particularly limited as long as the coagulation factor is activated by γ-glutamyl carboxylation or the activation response is received. Examples thereof include prothrombin (factor II), factor VII, factor IX, factor X, protein C, protein S, and protein Z.

In the embodiment of the present invention, the gene encoding GGCX (hereinafter, also referred to as "GGCX gene") is not particularly limited as long as it is a GGCX gene derived from desired biological species with GGCX. It is preferably a human GGCX gene, more preferably a gene encoding an amino acid sequence represented by SEQ ID NO.: 1. In this regard, the base sequence of human GGCX gene itself is known. For example, it is registered as the accession number EU847509 in the database provided from the National Center for Biotechnology Information (NCBI) of the U.S. National Library of Medicine. Alternatively, as the GGCX gene, a gene encoding mutant-type GGCX having a biological activity equal to that of the wild-type GGCX may be used.

In the embodiment of the present invention, the gene encoding NQO1 (hereinafter, also referred to as "NQO1 gene") is not particularly limited as long as it is an NQO1 gene derived from desired biological species with NQO1. It is preferably a human NQO1 gene, more preferably a gene encoding an amino acid sequence represented by SEQ ID NO.: 2. The base sequence of human NQO1 gene itself is known. For example, it is registered as the accession number AK312368 in the database provided from NCBI. Alternatively, as the NQO1 gene, a gene encoding mutant-type NQO1 which has a biological activity equal to that of the wild type NQO1 may be used.

The positions of the GGCX gene and the NQO1 gene in DNA of the recombinant baculovirus of the present invention are not particularly limited as long as the enzymes encoded by the above genes are expressed in a lepidopteran insect or cultured cell of the insect. Therefore, the GGCX and NQO1 genes may be successively inserted into the DNA of the recombinant baculovirus of the present invention or may be inserted into different positions apart from each other. When the genes are successively inserted into the baculovirus DNA, GGCX and NQO1 are expressed as a fusion protein. In this regard, it is not particularly limited which of the GGCX gene and the NQO1 gene is at the upstream. On the other hand, when the GGCX and NQO1 genes are inserted into different positions apart from each other in the baculovirus DNA, GGCX and NQO1 are expressed as distinct proteins. In the embodiment of the present invention, the GGCX and NQO1 genes are preferably inserted into different positions apart from each other in the baculovirus DNA.

In the embodiment of the present invention, the kind of baculovirus is not particularly limited as long as it is a virus with which a lepidopteran insect or cultured cell of the insect can be infected; however, a nuclear polyhedrosis virus (NPV) or its modified virus is preferred. Examples of the viruses include recombinant baculoviruses infective to hosts (*Bombyx mori* of the family Bombycidae and *Autographa californica* of the family Noctuidae) such as BmNPV, HycuNPV, AnpeNPV, and AcNPV (refer to JP-A No. 2003-52371). In a preferred embodiment, a cysteine protease defective (CPd) baculovirus is used (refer to Japanese Patent Application No. Hei 07-303488).

The recombinant baculovirus of the present invention may be produced by a known method in the art. Examples the method include a method comprising using a transfer vector capable of inserting a desired gene into the baculovirus DNA by homologous recombination. In the method, a recombinant baculovirus may be obtained by co-transfection of a transfer vector into which a desired gene is incorporated and a baculovirus DNA after linearization with a restriction enzyme with a cultured cell of a lepidopteran insect and screening of the infected cell.

In the embodiment of the present invention, the transfer vector is not particularly limited as long as it is a vector DNA which has a promoter capable of expressing a gene in a lepidopteran insect or cultured cell of the insect and can insert a desired gene into the downstream of the promoter. The transfer vector itself is known in the art. Examples thereof include pM02, pM23, pCPM, pYNG, pBM030, pBM050, and pVL1392. In this regard, the promoter can be appropriately selected from promoters known in the art. Examples thereof include polyhedrin promoter, p10 promoter, and *Bombyx mori* actin promoter.

When the recombinant baculovirus of the present invention is produced using the transfer vector, the GGCX and NQO1 genes may be incorporated into the same transfer vector or different transfer vectors. When the GGCX and NQO1 genes are incorporated into different transfer vectors, these two kinds of transfer vectors are preferably a combination of vectors which can incorporate the genes into different positions from each other in the baculovirus DNA. Examples of the combination of the vectors include a combination of a transfer vector capable of recombining the polyhedrin gene site in the baculovirus DNA with a desired gene and a transfer vector capable of recombining the cysteine protease gene site in the baculovirus DNA with a desired gene.

In the embodiment of the present invention, a protein secretory signal sequence may be fused to GGCX and NQO1, if necessary. That is, in the recombinant baculovirus of the present invention, a gene encoding a protein secretory signal sequence may be further incorporated into the upstream or downstream of each of the GGCX gene and the NQO1 gene. The protein secretory signal sequence may be appropriately selected from known sequences used in the expression system utilizing a lepidopteran insect, according to the kind of the recombinant vitamin K-dependent protein. Examples thereof include a prothrombin-derived secretory signal sequence (SEQ ID NO.: 3), a *Bombyx mori*-derived 30K signal sequence (SEQ ID NO.: 4), and a *Bombyx mori*-derived SP signal sequence (SEQ ID NO.: 5).

In the embodiment of the present invention, a functional tag may be fused to GGCX and NQO1, if necessary. That is, in the recombinant baculovirus of the present invention, a gene encoding a functional tag may be incorporated into the upstream or downstream of each of the GGCX gene and the NQO1 gene. As the kind of the functional tag, a tag for purifying proteins is particularly preferred. Examples thereof include FLAG, 6×His, glutation-S-transferase, and maltose binding protein tags.

In another embodiment of the present invention, a gene encoding a vitamin K-dependent protein may be further incorporated into a recombinant baculovirus into which the GGCX and NQO1 genes are incorporated. In this case, it is desirable that the gene encoding a vitamin K-dependent protein is expressably incorporated into a position apart from the GGCX and NQO1 genes in the baculovirus DNA. That is, the vitamin K-dependent protein is expressed as a distinct protein from GGCX and NQO1. According to the recombinant baculovirus, it is possible to express a large amount of the γ-glutamyl carboxylated vitamin K-dependent protein in a lepidopteran insect or cultured cell of the insect using the virus alone.

The scope of the present invention includes a host cell obtained by infecting a lepidopteran insect or cultured cell of the lepidopteran insect with the recombinant baculovirus of the present invention.

In the embodiment of the present invention, the lepidopteran insect is not particularly limited as long as it is a known lepidopteran insect suitable for expressing recombinant proteins. Examples thereof include *Bombyx mori, Spilosoma imparilis, Antheraea pernyi, Spodoptera frugiperda*, and *Trichoplusiani*. Among them, *Bombyx mori* is particularly preferred. In this regard, the lepidopteran insect may be at any stage of imago, pupa, and larva. From the viewpoint of the activity of serine protease, and the sensitivity to baculovirus, it is preferable to use a pupa or larva of the lepidopteran insect. Further, the cultured cell of the lepidopteran insect is not particularly limited as long as it is a cell line established from a lepidopteran insect suitable for expressing recombinant proteins. Examples thereof include BmN, BmN4, SpIm, Anpe, Sf9, Sf21, and High5.

The means for infecting the lepidopteran insect or cultured cell of the insect with the recombinant baculovirus of the present invention is not particularly limited, and it may be appropriately selected from known methods in the art. For example, in the case of infecting the lepidopteran insect, a method for injecting a solution containing the recombinant baculovirus into the insect is used. In the case of infecting the cultured cell, the solution containing the recombinant baculovirus may be added to a culture medium. If the lepidopteran insect or cultured cell of the insect is infected with the recombinant baculovirus and cultured for five to eight days, the recombinant protein is expressed in the host cell.

In the embodiment of the present invention, the lepidopteran insect or cultured cell of the lepidopteran insect is infected with the recombinant baculovirus into which the GGCX and NQO1 genes are incorporated, and then may be further infected with a recombinant baculovirus into which a desired gene encoding a vitamin K-dependent protein is incorporated.

The scope of the present invention also includes a kit for producing a recombinant vitamin K-dependent protein which contains the recombinant baculovirus into which a gene encoding GGCX and a gene encoding NQO1 are incorporated (hereinafter, simply referred to as "kit"). The recombinant baculovirus is the same as described in the recombinant baculovirus of the present invention.

In the embodiment of the present invention, it is preferable that the gene encoding a vitamin K-dependent protein is further incorporated into the recombinant baculovirus. In other words, three kinds of genes of the GGCX and NQO1 genes and the gene encoding a vitamin K-dependent protein are incorporated into the baculovirus DNA. The recombinant baculovirus of this embodiment is the same as described in the recombinant baculovirus of the present invention.

In another embodiment, it is preferable that the kit of the present invention further includes the recombinant baculovirus into which the gene encoding a vitamin K-dependent protein is incorporated. In this regard, the baculovirus may be produced in the same manner as in the baculovirus of the present invention except that the gene encoding a vitamin K-dependent protein is used as a desired gene. Here, the recombinant baculovirus into which the gene encoding GGCX and the gene encoding NQO1 are incorporated is also referred to as "first baculovirus". The recombinant baculovirus into which the gene encoding a vitamin K-dependent protein is incorporated is also referred to as "second baculovirus". In the kit of this embodiment, the first baculovirus and the second baculovirus may be stored in different containers, or both of them may be mixed and stored in one container. When the first baculovirus and the second baculovirus are mixed and stored, the mixing ratio thereof is not particularly limited, but they are preferably mixed so as to have a virus titer of 1:1.

The scope of the present invention includes a method for producing a recombinant vitamin K-dependent protein, comprising the step of expressing a γ-glutamyl carboxylated vitamin K-dependent protein in a lepidopteran insect or cultured cell of the insect using a recombinant baculovirus into which a gene encoding GGCX and a gene encoding NQO1 are incorporated (hereinafter, simply referred to as "production method"). In this regard, the recombinant baculovirus, the lepidopteran insect and cultured cell of the insect are the same as those described in the recombinant baculovirus of the present invention.

In the embodiment of the present invention, it is preferable that a gene encoding a vitamin K-dependent protein is further incorporated into the recombinant baculovirus. The recombinant baculovirus of this embodiment is the same as described in the recombinant baculovirus of the present invention. Alternatively, it is preferable to use the recombinant baculovirus into which the gene encoding GGCX and the gene encoding NQO1 are incorporated (first baculovirus) and the recombinant baculovirus into which the gene encoding a vitamin K-dependent protein is incorporated (second baculovirus).

In the production method of the present invention, the lepidopteran insect or cultured cell of the insect can be infected with the recombinant baculovirus to express the γ-glutamyl carboxylated vitamin K-dependent protein. The means for infecting the lepidopteran insect or cultured cell of the insect with the recombinant baculovirus is the same as described in the host cell of the present invention.

In the production method of the present invention, when the first baculovirus and the second baculovirus are used, the lepidopteran insect or cultured cell of the lepidopteran insect may be simultaneously infected with these baculoviruses. After being infected with one of the recombinant baculoviruses, the insect or cultured cell thereof may be infected with the other recombinant baculovirus. In this case, it is preferable to perform the second infection step within one week after the first infection step. The ratio of the amounts of the first baculovirus and the second baculovirus is not particularly limited. Preferably, the amounts are set to have a virus titer of 1:1.

Usually, the γ-glutamyl carboxylated vitamin K-dependent protein can be expressed by infecting the lepidopteran insect or cultured cell of the insect with the recombinant baculovirus and breeding or culturing the insect or cell for five to eight days. In the embodiment of the present invention, the means for obtaining a target protein from the lepidopteran insect or cultured cell of the insect in which the target protein is expressed is not particularly limited. For example, in the case of using a lepidopteran insect, the γ-glutamyl carboxylated vitamin K-dependent protein may be obtained by collecting a body fluid or crushing the insect to prepare a homogenate. In the case of using a cultured cell, the γ-glutamyl carboxylated vitamin K-dependent protein may be obtained by physically crushing the cell or dissolving the cell in a solution containing a cell dissolving agent such as a surfactant.

The production method of the present invention may further comprise the step of obtaining a soluble fraction containing the γ-glutamyl carboxylated vitamin K-dependent protein from the lepidopteran insect or the cultured cell thereof obtained in the expressing step, if necessary. The soluble fraction may be obtained by filtering or centrifuging the body fluid, homogenate, cell disrupted solution or cell lysate of the lepidopteran insect obtained in the above manner and separating the supernatant. In the centrifugation process, an appropriate buffer may be optionally added to a sample. The buffer is not particularly limited as long as it is a buffer suitable for storing a protein. Examples thereof include Tris buffers and phosphate buffers.

Hereinafter, the present invention will be described in detail with reference to Examples; however, the present invention is not limited to Examples.

EXAMPLES

Example 1

Investigation of Production and Expression of Recombinant Baculoviruses (1) Subcloning of Genes Encoding each of GGCX, NQO1, and VKOR On the basis of the base sequence of human GGCX gene (NCBI Acc. No. EU847509), the base sequence of human NQO1 gene (NCBI Acc. No. AK312368) and the base sequence of human VKOR gene (NCBI Acc. No. AY521634), which have been already reported, primer sets for subcloning the genes were designed. The base sequences of the primers are shown as follows. The base sequences of suitable restriction enzyme sites are added to the primers, respectively.

```
(i) GGCX gene primer set
F:
                                        (SEQ ID NO.: 6)
5'-GGGGTACCATGGCGGTGTCTGCCGGGTCCGC-3'

R:
                                        (SEQ ID NO.: 7)
5'-GCTCTAGAGAACTCTGAGTGGACAGGATCA-3'

(ii) NQO1 gene primer set
F:
                                        (SEQ ID NO.: 8)
5'-GAAGATCTATGGTCGGCAGAAGAGCACTGATCGTA-3'

R:
                                        (SEQ ID NO.: 9)
5'-GCTCTAGATTTTCTAGCTTTGATCTGGTTGTCAGTT-3'

(iii) VKOR gene primer set
F:
                                        (SEQ ID NO.: 10)
5'-GGGGTACCATGGGCAGCACCTGGGGGAGCCCT-3'

R:
                                        (SEQ ID NO.: 11)
5'-GCTCTAGATCAGTGCCTCTTAGCCTTGCCCTG-3'
```

The GGCX gene, the NQO1 gene, and the VKOR gene were isolated using the primer sets by the PCR method using a human liver cDNA library (Clontech) as a template. The isolated DNA fragments of the genes were purified using QIAquick (QIAGEN) and treated with restriction enzymes (GGCX: KpnI and XbaI, NQO1: XbaI, VKOR: KpnI and XbaI). Each of the resulting fragments was incorporated into a multi-cloning site of pM23 vector (SYSMEX CORPORATION). The resulting plasmid constructs are referred to as "pM-GGCX", "pM-NQO1", and "pM-VKOR", respectively. These plasmids are transfer plasmids for recombination with Polh site. After the restriction enzyme treatment, each of the DNA fragments was also incorporated into a multi-cloning site of pCPM vector (SYSMEX CORPORATION). The resulting plasmid constructs are referred to as "pCPM-GGCX", "pCPM-NQO1", and "pCPM-VKOR", respectively. These plasmids are transfer plasmids for recombination with CP site.

In all the transfer plasmids, a gene encoding a FLAG tag is incorporated into the downstream of the incorporated gene. Thus, the FLAG tag is fused to the C terminal of each protein expressed using each of the transfer plasmids.

(2) Production of Recombinant Baculoviruses
(2-1) Production of Single-Expressing Viruses Recombinant baculoviruses for singly expressing each of GGCX, NQO1, and VKOR were produced. These recombinant baculoviruses were produced by modifying the method of Maeda et al. (Invertebrate Cell system and Applications, Vol. 1, p. 167-181, CRC Press, Boca Raton (1989)). The specific procedure is as follows. First, the transfer plasmids for recombination with Polh site were purified using the plasmid purification kit (QIAGEN). Then, each transfer plasmid (0.5 µg) and DNA (0.2 µg) of CPd baculovirus (ATCC VR2500) after linearization were co-transfected into a BmN cell (Maeda, 1989) using a lipofection reagent (X-tremeGENE 9 DNA Transfection Reagent: Roche). Screening was performed by the limiting dilution method using a 96-well plate. The virus presented with the symptom of infection was selected and the culture supernatant was recovered. As a result, recombinant baculoviruses into which the GGCX gene, the NQO1 gene, and the VKOR gene were respectively incorporated were obtained. The resulting viruses are referred to as "GGCX single-expressing virus", "NQO1 single-expressing virus", and "VKOR single-expressing virus", respectively.

(2-2) Production of Co-Expressing Viruses

Recombinant baculoviruses for co-expressing each combination of GGCX and NQO1 as well as GGCX and VKOR were produced. The method described in (2-1) was modified to produce these recombinant baculoviruses. The specific procedure is as follows. The transfer plasmids for recombination with Polh site and the transfer plasmids for recombination with CP site were purified using the plasmid purification kit (QIAGEN). Then, each transfer plasmid for recombination with Polh site (0.5 µg), transfer plasmid for recombination with CP site (0.5 rig), and DNA (0.2 µg) of 5cut CPd baculovirus (ATCC VR2500) were co-transfected into a BmN cell (Maeda, 1989) using a lipofection reagent (X-tremeGENE 9 DNATransfection Reagent: Roche). Screening was performed by the limiting dilution method using a 96-well plate. The virus presented with the symptom of infection was selected and the culture supernatant was recovered. As a result, recombinant baculoviruses into which the GGCX gene, the NQO1 gene, and the VKOR gene were respectively incorporated were obtained. The resulting viruses are referred to as "GGCX/NQO1 co-expressing virus" and "GGCX/VKOR co-expressing virus", respectively.

(3) Investigation of Expression of Tag-Fused Prothrombin in BmN Cell

The supernatant was recovered to prepare a lysate of the BmN cell. The obtained lysate was analyzed by SDS-PAGE and Western blotting using an anti-FLAG antibody (Wako Pure Chemical Industries, Ltd.). The results are shown in FIG. 1. From FIG. 1, it was confirmed that proteins having molecular weights estimated to be GGCX, NQO1, and VKOR were expressed in the BmN lysate.

Example 2

Investigation of Expression and γ-Glutamyl Carboxylation of Vitamin K-Dependent Protein in *Bombyx mori*

(1) Subcloning of Genes Encoding Factor X and Prothrombin

On the basis of the base sequence of human factor X gene (NCBI Acc. No. BC_040125) (hereinafter also referred to as "hFX gene") and the base sequence of human prothrombin gene (NCBI Acc. No. NM_000506) (hereinafter also referred to as "hPTH gene") published on the database, primer sets for cloning the genes were designed. The sequences of the primers are shown as follows. The base sequences of suitable restriction enzyme sites are added to the primers, respectively.

```
(i) hFX gene primer set
F:
                                    (SEQ ID NO.: 12)
5'-AAGGTACCCGGGGATCCATGGGGCGCCCACTG-3'

R:
                                    (SEQ ID NO.: 13)
5'-AATCTAGATCACTTTAATGGAGAGGACGTTAT-3'

(ii) hPTH gene primer set
F:
                                    (SEQ ID NO.: 14)
5'-AAGAATTCATGGCCAACACCTTCTTGGAGGAG-3'

R:
                                    (SEQ ID NO.: 15)
5'-AATCTAGACTACTCTCCAAACTGATCAATGACCTT-3'
```

The hFX gene and the hPTH gene were isolated using the primer sets by the PCR method using a human liver cDNA library (Clontech) as a template. The isolated DNA fragments were purified using QIAquick (QIAGEN) and treated with restriction enzymes KpnI and XbaI. Each of the resulting fragments was incorporated into a multi-cloning site of pM23 vector (SYSMEX CORPORATION). The resulting plasmid constructs are referred to as "pM-FX" and "pM-PTH", respectively.

(2) Production of Recombinant Baculoviruses

Recombinant baculoviruses for singly expressing each of the factor X and prothrombin were produced. These recombinant baculoviruses were produced using pM-FX and pM-PTH in the same manner as described in (2-1) of Example 1. Thus, recombinant baculoviruses into which the factor X gene and the prothrombin gene were respectively incorporated were obtained. The resulting viruses are referred to as "FX single-expressing virus" and "PTH single-expressing virus", respectively.

Figures 2A, 2B:
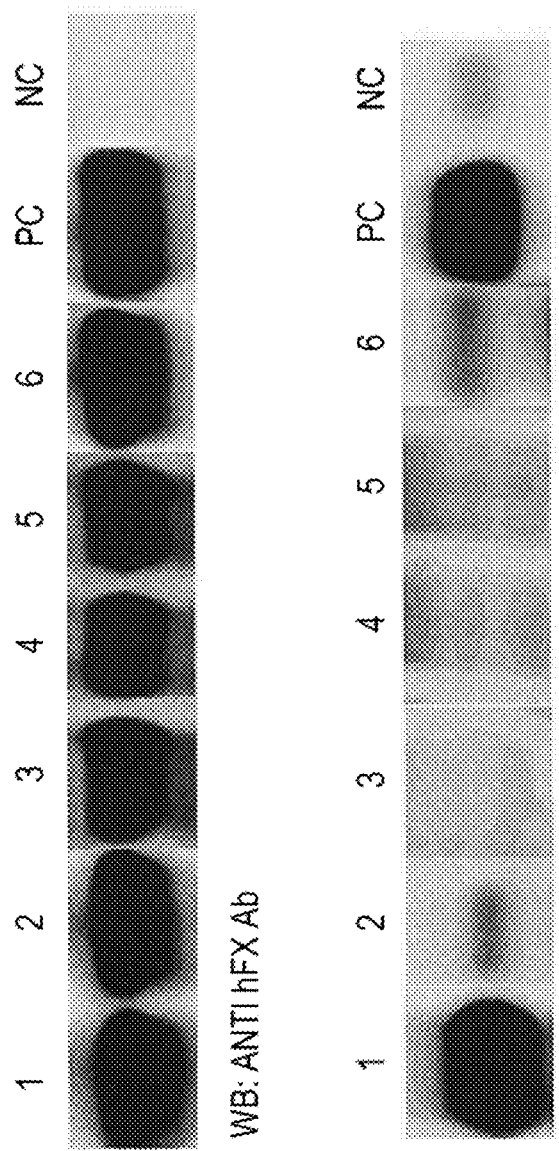
FIG. 2A shows photographs illustrating the expression levels of human factor X in *Bombyx mori* larvae infected with various recombinant baculoviruses produced in Example 1 and the recombinant baculovirus for expressing human factor X.
FIG. 2B shows photographs illustrating the degrees of γ-glutamyl carboxylation of the expressed human factor X.

(3) Expression and γ-Glutamyl Carboxylation of Vitamin K-Dependent Protein (3-1) Human Factor X (i) Investigation of Expression and γ-Glutamyl Carboxylation of Human Factor X The FX single-expressing virus, and each of the expressed viruses produced in Example 1 were mixed so as to have a virus titer of 1:1. The resulting mixture was inoculated into larvae of *Bombyx mori* (variety: Kinsyu-showa, silkworm seeds were purchased from Ueda-sanshu and developed artificially to larvae in SYSMEX CORPORATION). As the control, only the FX single-expressing virus was inoculated into the larvae of *Bombyx mori*. The body fluid was extracted from the infected larvae seven days after the virus inoculation. In order to confirm the expression level of the factor X, a part of the resulting body fluid was analyzed by SDS-PAGE and Western blotting using an anti-Factor X antibody (Enzyme research Laboratories). In order to detect the γ-glutamyl carboxylated factor X, the resulting body fluid was immunoprecipitated using an anti-Gla-domain antibody (SEKISUI MEDICAL CO., LTD.). The resulting precipitates were analyzed by SDS-PAGE and Western blotting using an anti-Factor X antibody (Enzyme research Laboratories). The results are shown in FIG. 2. The samples of the test plots of FIG. 2 are as follows.

Test plot 1: GGCX/NQO1 co-expressing virus and FX single-expressing virus
Test plot 2: GGCX/VKOR co-expressing virus and FX single-expressing virus
Test plot 3: GGCX single-expressing virus and FX single-expressing virus
Test plot 4: NQO1 single-expressing virus and FX single-expressing virus
Test plot 5: VKOR single-expressing virus and FX single-expressing virus
Test plot 6: FX single-expressing virus
PC: naturally-occurring human factor X (Haematologic Technologies)
NC: uninfected *Bombyx mori* larva body fluid From FIG. 2A, it was found that the bands were confirmed in all the test plots 1 to 6 and thus a large difference among the expression levels of the factor X was not observed. From FIG. 2B, in the sample (test plot 1) infected with the FX single-expressing virus and the GGCX/NQO1 co-expressing virus, a significantly higher signal as compared to the other samples (test plots 2 to 6) was obtained. As a result, it was suggested that when GGCX and NQO1 and the factor X were co-expressed in the *Bombyx mori* larvae, the γ-glutamyl carboxylated factor X was efficiently obtained.

(ii) Investigation of Expression Level of Human Factor X

The concentration of human factor X contained in the body fluid of *Bombyx mori* larvae infected with the GGCX/NQO1 co-expressing virus and the FX single-expressing virus was measured by the Sandwich ELISA method using the human Factor X ELISA kit (Assaypro). As a result, it was found that about 500 μg/ml of the human factor X was contained in the body fluid. The recovery amount of the body fluid per larva of *Bombyx mori* is about 0.4 ml. Accordingly, the expression level per larva of *Bombyx mori* is estimated to be about 200 μg.

(3-2) Regarding Human Prothrombin

The PTH single-expressing virus and the GGCX/NQO1 co-expressing virus were mixed so as to have a virus titer of 1:1. The resulting mixture was inoculated into pupae of *Bombyx mori* (variety: Kinsyu-showa, silkworm seeds were purchased from Ueda-sanshu and developed artificially to pupae in SYSMEX CORPORATION). As the control, only the PTH single-expressing virus was inoculated into the larvae of *Bombyx mori*. The infected pupae were recovered seven days after the virus inoculation and frozen at −80° C. The frozen pupae were crushed with a blender. The pupae residues in the resulting crushed solution were removed by low-speed centrifugation treatment and filtration to give a homogenate. In order to confirm the expression level of prothrombin, a part of the resulting homogenate was analyzed by SDS-PAGE and Western blotting using an anti-thrombin antibody (Novus). In order to detect the γ-glutamyl carboxylated prothrombin, the resulting body fluid was immunoprecipitated using an anti-Gla-domain antibody (SEKISUI MEDICAL CO., LTD.). The resulting precipitates were analyzed by SDS-PAGE and Western blotting using an anti-thrombin antibody (Novus). The results are shown in FIG. 3. The samples of the test plots of FIG. 3 are as follow.

Test plot 1: GGCX/NQO1 co-expressing virus and PTH single-expressing virus

Test plot 2: PTH single-expressing virus

PC: naturally-occurring human prothrombin (derived from human plasma, Calbiochem)

NC: uninfected *Bombyx mori* homogenate

Figure 3A:
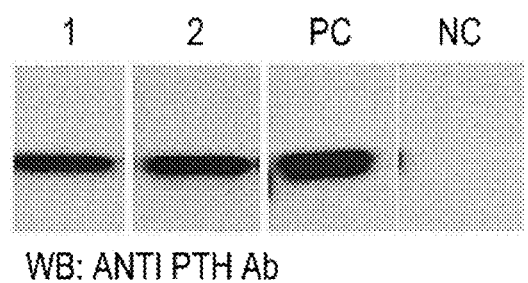
FIG. 3A shows photographs illustrating the expression levels of human prothrombin in pupae infected with the recombinant baculoviruses for co-expressing GGCX and NQO1 and the recombinant baculovirus for expressing human prothrombin.
Figure 3B:
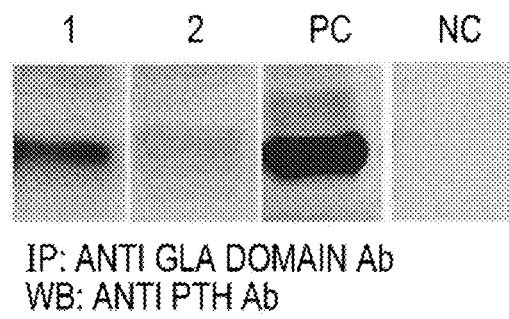
FIG. 3B shows photographs illustrating the degrees of γ-glutamyl carboxylation of the expressed human prothrombin.

From FIG. 3A, it was found that the bands were confirmed in both the test plots 1 and 2 and thus a large difference among the expression levels of prothrombin was not observed. From FIG. 3B, in the sample (test plot 1) infected with the PTH single-expressing virus and the GGCX/NQO1 co-expressing virus, a significantly higher signal as compared to the other sample (test plot 2) was obtained. As a result, it was suggested that when GGCX and NQO1 and prothrombin were co-expressed in the *Bombyx mori* pupae, the γ-glutamyl carboxylated prothrombin was efficiently obtained.

Example 3

Investigation of Conditions of γ-Glutamyl Carboxylation of Vitamin K-Dependent Protein in *Bombyx mori*

The FX single-expressing virus produced in Example 2 and each of the expressed viruses produced in Example 1 were mixed so as to have the following virus titer. The resulting mixture was inoculated into larvae of *Bombyx mori* (variety: Kinsyu-showa, silkworm seeds were purchased from Ueda-sanshu and developed artificially to larvae in SYSMEX CORPORATION) (test plots 1 to 4). As the control, only the FX single-expressing virus was inoculated into the larvae of *Bombyx mori* (test plot 5).

The body fluid was extracted from the infected larvae seven days after the virus inoculation. In order to confirm the expression level of the factor X, a part of the resulting body fluid was analyzed by SDS-PAGE and Western blotting using an anti-Factor X antibody (Enzyme research Laboratories). In order to detect the γ-glutamyl carboxylated factor X, the resulting body fluid was immunoprecipitated using an anti-Gla-domain antibody (SEKISUI MEDICAL CO., LTD.). The resulting precipitates were analyzed by SDS-PAGE and Western blotting using an anti-Factor X antibody (Enzyme research Laboratories). The results are shown in FIG. 4. The samples of the test plots of FIG. 4 are as follows.

Test plot 1: GGCX single-expressing virus: NQO1 single-expressing virus: FX single-expressing virus=1:1:1

Test plot 2: GGCX single-expressing virus: VKOR single-expressing virus: FX single-expressing virus=1:1:1

Test plot 3: GGCX single-expressing virus: NQO1 single-expressing-virus: VKOR single-expressing virus: FX single-expressing virus=1:1:1:1

Test plot 4: GGCX/NQO1 co-expressing virus: FX single-expressing virus=1:1

Test plot 5: FX single-expressing virus

PC: naturally-occurring human factor X (Haematologic Technologies)

Figure 4A:
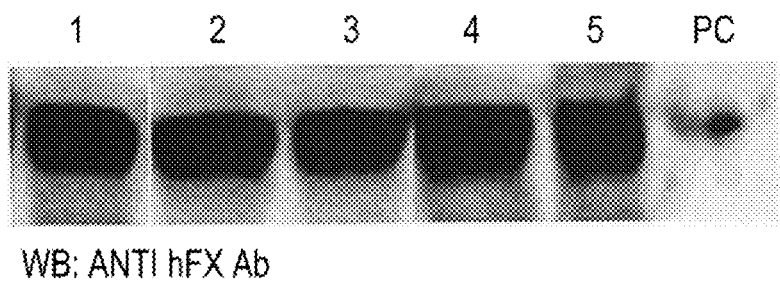
FIG. 4A shows photographs illustrating the expression levels of human factor X in *Bombyx mori* larvae infected with various recombinant baculoviruses produced in Example 1 and the recombinant baculovirus for expressing human factor X.
Figure 4B:
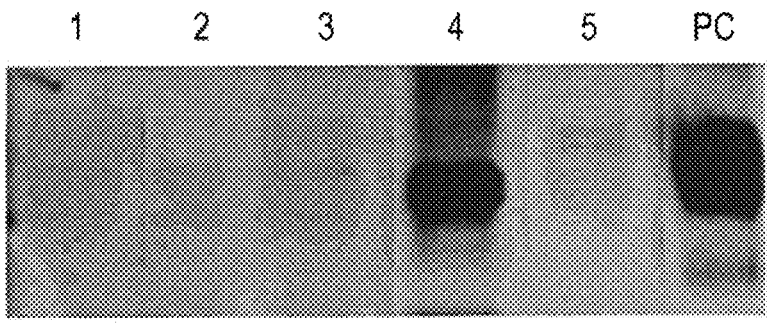
FIG. 4B shows photographs illustrating the degrees of γ-glutamyl carboxylation of the expressed human factor X.

From FIG. 4A, it was found that the bands were confirmed in all the test plots 1 to 5 and thus a large difference among the expression levels of the factor X was not observed. From FIG. 4B, in the sample (test plot 1) infected with the FX single-expressing virus and the GGCX/NQO1 co-expressing virus, a significantly higher signal as compared to the other samples (test plots 1 to 3 and 5) was obtained. As a result, it was found that the γ-glutamyl carboxylated factor X was hardly obtained in the expression system using baculoviruses for singly expressing each of the factors (GGCX, NQO1, and VKOR) involved in γ-glutamyl carboxylation and the factor X in *Bombyx mori* larvae. Therefore, it was shown that it is necessary to use the GGCX/NQO1 co-expressing virus in which the GGCX gene and the NQO1 gene are incorporated into the same baculovirus, in order to efficiently obtain the γ-glutamyl carboxylated factor X.

What is claimed is:

1. A recombinant baculovirus, wherein a gene encoding γ-glutamyl carboxylase (GGCX) and a gene encoding DT-diaphorase (NQO1) are incorporated into a genome of the recombinant baculovirus.

2. The recombinant baculovirus according to claim 1, wherein a gene encoding a vitamin K-dependent protein is further incorporated into the genome of the recombinant baculovirus.

3. The recombinant baculovirus according to claim 2, wherein the vitamin K-dependent protein is a vitamin K-dependent blood coagulation factor.

4. The recombinant baculovirus according to claim 3, wherein the vitamin K-dependent blood coagulation factor is selected from the group consisting of prothrombin, factor VII, factor IX, factor X, protein C, protein S, and protein Z.

5. A host cell, which is obtained by infecting a lepidopteran insect or cultured cell of the lepidopteran insect with the recombinant baculovirus according to claim 1.

6. The host cell according to claim 5, wherein the Lepidopteran insect is *Bombyx mori*.

7. A kit for producing a recombinant vitamin K-dependent protein, comprising a recombinant baculovirus, wherein a gene encoding GGCX and a gene encoding NQO1 are incorporated into a genome of the recombinant baculovirus.

8. The kit according to claim 7, further comprising a second recombinant baculovirus, wherein a gene encoding vitamin K-dependent protein is incorporated into a genome of the second recombinant baculovirus.

9. The kit according to claim 7, wherein a gene encoding a vitamin K-dependent protein is further incorporated into the genome of the recombinant baculovirus.

10. A method for producing a recombinant vitamin K-dependent protein, comprising expressing a γ-glutamyl carboxylated vitamin K-dependent protein in a lepidopteran insect or cultured cell of the lepidopteran insect that expresses a γ-glutamyl carboxylated vitamin K-dependent protein and has been infected with a recombinant baculovirus, wherein a gene encoding GGCX and a gene encoding NQO1 are incorporated into a genome of the recombinant baculovirus.

11. The method according to claim 10, wherein the lepidopteran insect or cultured cell of the lepidopteran insect expressing the γ-glutamyl carboxylated vitamin K-dependent protein comprises a second recombinant baculovirus, wherein a gene encoding the vitamin K-dependent protein is incorporated into a genome of the second recombinant baculovirus.

12. The method according to claim 10, wherein a gene encoding a vitamin K-dependent protein is further incorporated into the genome of the recombinant baculovirus.

13. The method according to claim 10, wherein, in the expressing step, a γ-glutamyl carboxylated vitamin K-dependent protein is expressed in the lepidopteran insect.

14. The method according to claim 11, wherein, in the expressing step, a γ-glutamyl carboxylated vitamin K-dependent protein is expressed in the lepidopteran insect.

15. The method according to claim 12, wherein, in the expressing step, a γ-glutamyl carboxylated vitamin K-dependent protein is expressed in the lepidopteran insect.

16. The method according to claim 13, wherein, in the expressing step, a γ-glutamyl carboxylated vitamin K-dependent protein is expressed in a lava or pupa of the lepidopteran insect.

17. The method according to claim 10, wherein the Lepidopteran insect is *Bombyx mori*.

* * * * *